US 6,987,898 B2

(12) United States Patent
Tran et al.

(10) Patent No.: US 6,987,898 B2
(45) Date of Patent: Jan. 17, 2006

(54) MOLECULAR DETECTION USING AN OPTICAL WAVEGUIDE FIXED TO A CANTILEVER

(75) Inventors: Alex T. Tran, Madison, NJ (US); Dustin W. Carr, Pittstown, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 159 days.

(21) Appl. No.: 10/625,384

(22) Filed: Jul. 23, 2003
(Under 37 CFR 1.47)

(65) Prior Publication Data
US 2005/0018946 A1    Jan. 27, 2005

(51) Int. Cl.
*G02B 6/00*    (2006.01)
(52) U.S. Cl. .................. 385/13; 385/12; 73/64.43; 73/800; 356/73.1
(58) Field of Classification Search .............. 385/12, 385/13; 356/73.1; 73/53.01, 64.43, 800
See application file for complete search history.

(56) References Cited

U.S. PATENT DOCUMENTS

| | | | |
|---|---|---|---|
| 5,671,303 A | 9/1997 | Shieh et al. | 385/12 |
| 5,807,758 A | 9/1998 | Lee et al. | 436/526 |
| 5,982,009 A | 11/1999 | Hong et al. | 257/414 |
| 6,269,685 B1 * | 8/2001 | Oden | 73/54.3 |
| 6,346,376 B1 | 2/2002 | Sigrist et al. | 435/5 |
| 6,436,647 B1 | 8/2002 | Quate et al. | 435/6 |
| 6,575,020 B1 * | 6/2003 | de Charmoy Grey et al. | 73/54.23 |
| 2002/0074513 A1 | 6/2002 | Abel et al. | 250/458.1 |

OTHER PUBLICATIONS

Alvarez et al., 2003, "Development of Nanomechanical Biosensor for Oligonucleotide Hybridization Detection," web page accessed Apr. 24, 2003 at www.imm.cnm.csic.es/biosensores/home.
Baller et al., 2000, Ultramicroscopy 82:(1-4) 1-9 (Abstract only).
"Development and Fabrication of a Nanobichip based on Microcantilevers," web page, accessed Apr. 24, 2003 at www.imm.cnm.csic.es/biosensores/cantilever- development.htm.
Fritz et al., 2000, Science, 288:316-318.
Gimzewski, 2003, "Translating Biochemical Recognition into Nanomechanical Action," web page, accessed Apr. 24, 2003 at www.chem.ucla.edu/dept/Faculty/gimzewski/id11.htm.
Grogan et al., 2002 Biosens. Bioelectron. 17(3):201-207 (Abstract only).
Hofmann et al., 2002 Anal. Chem. 74 (20): 5243-5250 (Abstract only).
Institute of Microsystem Technologies, web page, "PECVD Process" accessed Apr. 15 2003 at www.uni-siegen.de/ihe/forschung/pecvd-e.htm.
Lavrik et al., 2003, Appl. Phys. Lett. Apr. 21, 2003 (Abstract and Figure only).
LioniX BV, 2003, web page, "PECVD Silicon Technology" (SiOxNy), accessed Apr. 15, 2003 at www.lionphotonix.nl/technology/processes_pecvdsioxny.html.

(Continued)

*Primary Examiner*—Akm Enayet Ullah
*Assistant Examiner*—Daniel Petkovsek (57) ABSTRACT

The invention relates to devices and methods for detecting a ligand in a liquid, based on deflection of one or more microscopic cantilevers. Each cantilever has an optical waveguide fixed thereto or integral therewith. Deflection of the cantilever is detected by assessing coupling of light between the optical waveguide on the cantilever and an optical waveguide fixed distally thereto.

20 Claims, 1 Drawing Sheet

OTHER PUBLICATIONS

LioniX-Sion Technology, web page, "Sion Technology", accessed Apr. 15, 2003 at www.lionixbv.nl/technology/lio_sion.html.

McKendry et al., 2002, Proc. Natl. Acad. Sci. USA 99:(15) 9783-9788.

"Methods of Controlled Immobilization at DNA Probes," web page, accessed Apr. 24, 2003 at www.imm.cnm.csic.es/biosensores/cantilever-Immobilization.htm.

MicroVacuum, Ltd., 2003, catalog entry OW 2400c, accessed Apr. 15, 2003 at www.microvacuum.com/products/biosensor/.

MicroVacuum, Ltd., 2003, catalog entry OW 3200, accessed Apr. 14, 2003, at www.microvacuum.com/products/biosensor/OW3200.asp.

Moulin et al., 1999, Langmuir 15:8776-8779.

Moulin et al., 2000 Ultramicroscopy 82:(1-4):23-31 (Abstract only).

Raiteri et al, 2000, Electrochim. Acta 46:157-163.

Stimpson et al., 1995, Proc. Natl. Acad. Sci. USA 92:6379-6383.

"Synthesis of Silicon Oxynitride Films on Porous Substrates" web page, accessed Apr. 15, 2003 at www.icmm.csic.es/fis/english/oxinitruro_de_silicio.html.

Tamayo et al., 2001, Ultramicroscopy 86:167-173.

Wu et al., 2001, Nat. Biotechnol. 19:856-860.

Wu et al., 2001, Proc. Natl. Acad. Sci. USA 98(4):1560-1564.

* cited by examiner

MOLECULAR DETECTION USING AN OPTICAL WAVEGUIDE FIXED TO A CANTILEVER

TECHNICAL FIELD

The invention relates generally to the field of detecting molecules using microscopic cantilever-based devices.

BACKGROUND OF THE INVENTION

Detection of a molecule, e.g., a nucleic acid, a polypeptide, a carbohydrate, or a combination thereof, or binding between a molecule and a binding partner of the molecule is a common assay technique. Many molecular detection techniques are limited by low a concentration of the molecule, a relatively high concentration of similar molecules, difficulty in isolating the molecule, and similar drawbacks. As a result, many known molecular detection techniques are difficult or impossible to perform, and results obtained using such methods can be inaccurate. A drawback shared by most prior detection methods is that they require that a member of the binding pair, or the bound pair, be detectably labeled. In addition to increasing the labor requirement and complexity of the test, such labeling can interfere with the assay results.

Nanomechanical biodetection devices and methods have recently been developed by others, e.g., Fritz et al., 2000, Science 288:316–318, and do not require labeling of receptors or ligands. In prior art devices, a micrometer-scale cantilever is formed from a material that reflects light, and one member of a receptor-ligand binding pair is immobilized on a face of the cantilever. Binding of the other pair member with the immobilized pair member induces a stress on the face of the cantilever having the immobilized pair member thereon, resulting in bending of the cantilever. Bending of the cantilever is detected in prior art systems by a change in the path of light reflected off a distal portion of the cantilever.

A difficulty experienced using nanoscale cantilever-based binding detectors based on reflected light is that the devices are highly sensitive to minute vibrations. Any misalignment of the optical beam severely degrades the optical signal. Also, use of an external optical source and reader with an array of nanoscale cantilevers requires reliable and highly accurate repositioning of the light source, the detector, the array, or some combination of these. Apart from the need for precise mechanical actuators to perform those manipulations, the manipulations themselves prevent parallel real-time detection of multiple biomaterials. Prior art methods of using nanoscale cantilever microarrays also require precise positioning of optical components relative to the array.

BRIEF SUMMARY OF THE INVENTION

The invention is a microscopic cantilever-based detector for detecting a ligand in a fluid, i.e., a liquid or a gas, based on assessing light coupling between ends of an optical waveguide. The detector has a first body and a second body having a cantilever extending therefrom into a gap between the first and second bodies. An optical waveguide extends across the first and second bodies and across the cantilever. The waveguide is interrupted by a gap that coincides with a gap between the first and second bodies. The cantilever has two substantially parallel planar faces, and one of the two faces has a receptor that binds specifically with the ligand immobilized thereon. When the ligand binds with the receptor, bending of the cantilever is induced by surface forces exerted on the cantilever face. When the cantilever bends, the gapped ends of the waveguide become misaligned, and light coupling across the gap of the waveguide decreases. Decreased light coupling can be detected and indicates that the ligand is present in the fluid. The concentration of the ligand can be assessed by measuring the degree of decoupling of light across the gap of the waveguide.

The waveguide can be integral with the cantilever or attached thereto. Alternatively, the waveguide can rest upon or otherwise contact the second body in a configuration such that deflection of the cantilever reduces light coupling of the gapped ends of the waveguide.

The first body, the second body, or both can have a cladding material applied thereto or integral therewith, to improve light transmission through the waveguide.

The first and second bodies can be fabricated from substantially any material. The two bodies can be integral parts of a single substrate, or they can be separate pieces. A first metallic layer can be interposed between the receptor and the face of the cantilever in order to facilitate immobilization of the receptor on the cantilever. A second metallic layer can be interposed between the first metallic layer and the face of the cantilever, to enhance bonding between the cantilever face and the first metallic layer.

The shape of the cantilever is within the implementer's discretion. Examples of suitable shapes include substantially rectangular cantilevers and those that are wedge- or V-shaped. Temperature-induced fluctuations in cantilever deflection can be avoided by maintaining the cantilever (or the entire detector) at substantially the same temperature as the fluid.

If the detector has a plurality of cantilevers, then the detector can be used to detect multiple ligands in the fluid at the same time.

In operation of the detector, the ends of the waveguide distal from the gap are coupled with a light source and a light detector. Detection of light coupling across the waveguide gap can be detected in any known way. For instance, the intensity of light coupled across the gap can be measured. Light coupling decreases as the cantilever is bent. In one embodiment, the detector has a device coupled with the cantilever for inducing a regular vibration of the cantilever. In that embodiment, the frequency of vibration of the cantilever can be assessed by the frequency of light coupling across the gap. Binding between the ligand and the receptor alters the resonant frequency of vibration of the cantilever. A change in that resonant frequency indicates binding between the ligand and the receptor.

BRIEF SUMMARY OF THE SEVERAL VIEWS OF THE DRAWINGS

FIG. 1, consisting of FIGS. 1A, 1B, and 1C, are top, front, and side orthographic projections, respectively, of an example of the detector described herein, wherein the first and second bodies are fabricated from a unitary substrate.

DETAILED DESCRIPTION OF THE INVENTION

Figure 1A:
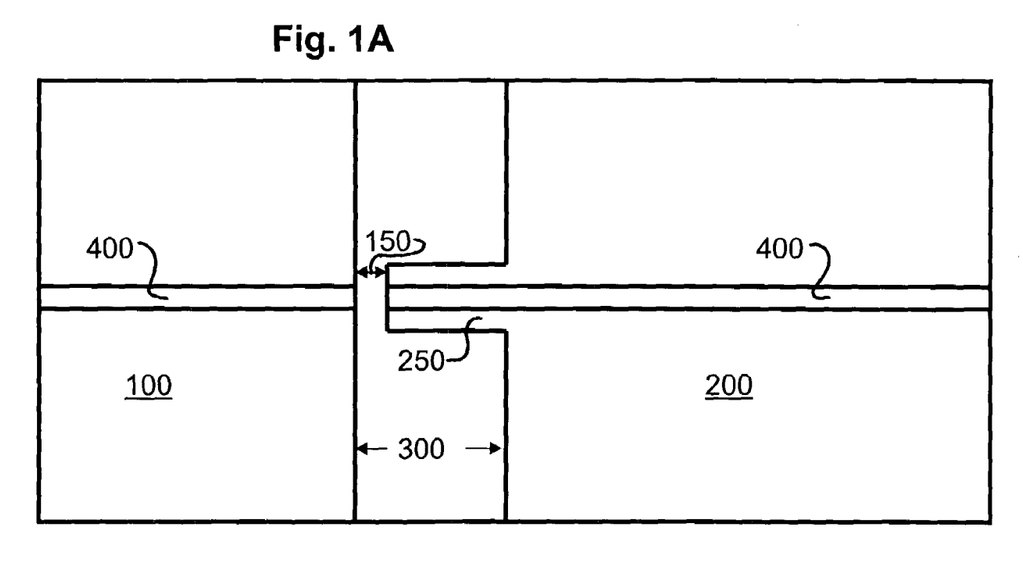
Figure 1B:
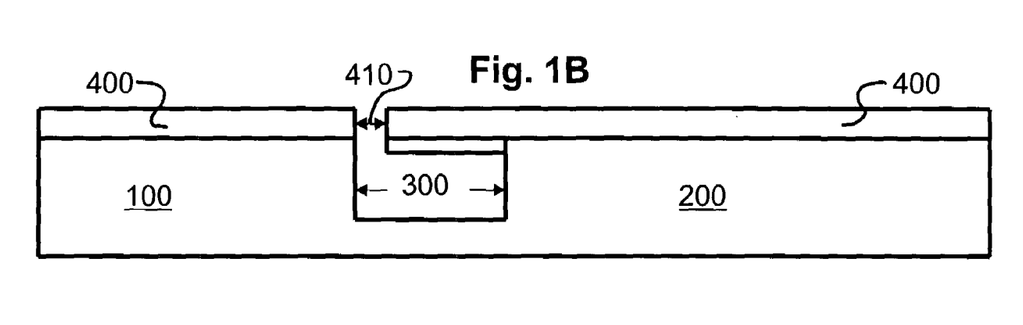
Figure 1C:
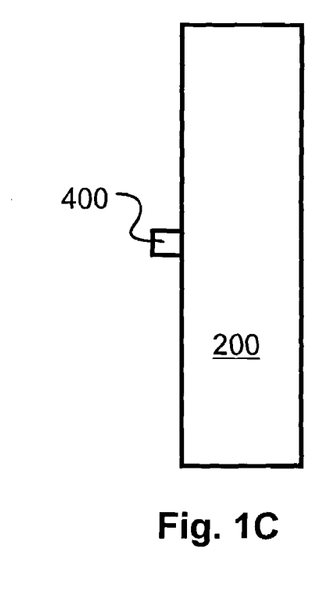

The invention relates to discovery of an improved method of assessing occurrence of a compound in a fluid using a microscopic cantilever-based device. Unlike prior art devices in which cantilever deflection is detected by assessing reflection or refraction of a light beam directed at a portion of the cantilever surface, the detector described herein employs an optical waveguide 400 that extends along the cantilever 250. The waveguide has a gap 410 in it, and this gap coincides with the gap 150 between the distal end of the cantilever and another body located beyond the distal end of the cantilever. In its non-deflected position, the cantilever supports the waveguide so that the ends of the waveguide are aligned in a light-coupling manner, e.g., butt-coupled wherein the waveguide portions are aligned end-to-end and the ends of the waveguide portion are substantially normal to the long axis of the waveguide, across the gap 410. In this configuration, relatively efficient coupling of light occurs through the waveguide and across the waveguide gap 410. If the cantilever is deflected, the ends of the waveguide adjacent the gap 410 become non-aligned (increasingly so as deflection of the cantilever increases) and light coupling across the waveguide gap 410 is less efficient (and becomes increasingly less efficient as deflection of the cantilever increases).

This invention can be used in conjunction with substantially any known technology for immobilizing a receptor to the surface of a microscopic cantilever. Many such technologies are known, whereby binding between the immobilized receptor and a ligand thereof induces surface stress on the cantilever, thereby inducing bending of the cantilever. Prior art systems detected cantilever deflection by detecting light reflected off the cantilever (or off a diffractional grating thereon). Those prior art systems were, for that reason, extremely sensitive to minute vibration, to mispositioning or misdirection of the external light generation or detection devices, and to other perturbations. The detector described herein is significantly less sensitive to such perturbations and can, if desired be used to assess occurrence in a fluid of multiple compounds in real time.

As used herein, each of the following terms delimited with quotation marks has the meaning associated with it.

A "receptor-ligand pair" is a pair of molecules which bind with one another in a way that is specifically dependent on the identity of the molecules, i.e., the molecules bind with one another to a significantly greater degree than they do with different molecules or unrelated types of molecules.

A "detection assay" is a test intended to assess whether a compound is present in a fluid, the concentration of the compound in the fluid, or both.

An "optical waveguide" is an elongated structure that is made from a substantially optically transparent material and that is capable of guiding light in a direction parallel to the long axis of the waveguide, while substantially confining the light to a region within its surfaces.

An optical waveguide is "butt-gapped" if the light-conveying matrix of the waveguide is interrupted by a gap and the faces of the interrupted waveguide are substantially parallel to one another.

Waveguides having ends separated by a gap (or portions of a single, gapped waveguide) are "coupled" if light conveyed along the waveguide(s) is transmitted across the gap with relatively little loss, such as not more than 50% loss of intensity, e.g., not more than 3 decibel loss, and preferably not more than 1 decibel loss.

The invention relates to a detector for detecting a ligand in a fluid and to methods of making and using such a detector. Like prior art microscopic cantilever-based detectors, the detector described herein involves a cantilever having a receptor immobilized thereon, such that the cantilever bends when a ligand of the receptor binds therewith. Whereas deflection of the cantilever in prior art devices was detected by directing a beam of light, e.g., a laser, at one of the large, planar surfaces of the cantilever and detecting reflection or diffraction of the directed light, the detector described herein does not depend on reflection or diffraction of light by the cantilever surface. Instead, a cantilever 250 of the device described herein has an optical waveguide 400 fixed to it, e.g., integral with the cantilever or bonded to a surface thereof. When the cantilever is in its non-deflected, i.e., straight, position, the waveguide couples light conveyed therein into another waveguide fixed to, e.g., integral with a first body located distally from the cantilever and separated therefrom by a gap 150. When the cantilever is deflected, the waveguide fixed to the cantilever is displaced, and it conveys light less efficiently (or not at all) to the waveguide fixed to the first body. In this way, deflection of the cantilever can be detected.

The cantilever 250 of the device can be substituted with one member of substantially any receptor-ligand pair and used to detect the other member of the pair. By way of example, binding of an antibody with its corresponding antigen can be detected, as can hybridization of polynucleotides having complementary sequences. Numerous methods are described in the art for immobilizing such components on cantilever surfaces and other materials from which cantilevers can be fabricated, e.g., U.S. Pat. No. 6,436,647; Stimpson et al., 1995, Proc. Natl. Acad. Sci. USA 92:6379–6383; McKendry et al., 2002, Proc. Natl. Acad. Sci. USA 99(15): 9783–9788; Baller et al., 2000, Ultramicroscopy 82(1–4):1–9; Moulin et al., 2000, Ultramicroscopy 82(1–4):23–31.

A plurality of cantilevers 250 having optical waveguides 400 fixed thereto and substituted with the same molecule can be incorporated into a single device. Such multi-cantilever devices can provide duplicate assessments of occurrence of a single molecule in a fluid contacted with the cantilevers. Alternatively, two or more of the cantilevers in a single detector can be substituted with different molecules, e.g., members of different receptor-ligand pairs, so that occurrence of a plurality of molecules can be assessed, e.g., simultaneously or sequentially, in a fluid provided to the detector. Alignment of the optical waveguides fixed to different cantilevers with their corresponding waveguides fixed to the body(ies) can be assessed sequentially, in parallel, or some combination thereof, as desired.

The detector described herein is useful for rapid detection of specific molecules in a wide variety of environments and circumstances. The specificity of the detector for a particular molecule will depend on the identity of the receptor immobilized on the surface of a cantilever 250 of the detector. The specificity of receptor-ligand binding can be selected such that substantially only a single molecule, e.g., the antigen of a selected antibody or a polynucleotide that is completely complementary, will bind with the receptor. Alternatively, the specificity can be selected such that the receptor that will bind with a variety of ligands. By way of example, a receptor can be a polynucleotide population comprising polynucleotides having sequences that are identical except at one nucleotide residue, at which either of two alternative residues occurs, i.e., for detection of either form of the complementary polynucleotide.

Operation of a detector described herein is relatively simple. A fluid, i.e., a liquid or a gas, is provided to the device in such a way that the fluid contacts at least one cantilever 250 of the device. If a ligand that binds with the receptor immobilized on the cantilever is present in the fluid, then it binds with the receptor and the cantilever bends. Deflection of the cantilever is assessed by detecting a change in the efficiency of light conveyance from the waveguide 400 fixed to the cantilever to the waveguide 400 fixed to the first body. The exact arrangement of the detector can vary, and is within the discretion of the implementer. However, the device should be made in a way that facilitates contact of the fluid with every cantilever to be used for ligand detection. In one embodiment, the detector is fabricated in a standardized format made to fit into an apparatus that provides light to one end of the waveguide(s) of the detector and detects light transmitted through the detector to the other end of the waveguides thereof. Such a standardized format permits an operator to use a single instrument comprising larger or more expensive components, e.g., a laser and a light detector with a variety of relatively inexpensive detector units which can be adapted for detection of different molecules or for use with only a single fluid sample.

The detector described herein includes a first body 100 and a second body 200 that are separated by a gap 300. The second body has a cantilever 250 extending therefrom into the gap 300 between the first and second bodies. The cantilever has at least two parallel planar faces, e.g., the "top" and "bottom" of the cantilever, although the detector can be operated with the cantilever oriented in substantially any direction. An optical waveguide 400 extends across, i.e., along a surface of, or through the first and second bodies, including along the length of the cantilever. The optical waveguide has a gap 410 therein, coinciding with the gap 150 between the distal end of the cantilever and the first body 100, i.e., a portion of gap 300. A receptor is immobilized on one of the planar faces of the cantilever, but not on the other. Binding between the receptor and a ligand of the receptor induces a surface stress on the face of the cantilever, which causes the cantilever to bend, thereby deflecting the distal end of the cantilever, relative to its position in the absence of the ligand.

The distal end of the waveguide 400 fixed to the cantilever 250 and the end of the waveguide 400 fixed to the first body 100 at the edge nearest the cantilever are arranged and shaped such the waveguides are coupled when the cantilever is in the non-deflected position. Deflection of the cantilever, i.e., and the waveguide fixed thereto, is detected by assessing the amount of light transmitted across the gap 410 (or by assessing the efficiency of coupling). A change in this value indicates deflection of the waveguide. If the initial degree of alignment of the waveguides and the geometry of the gapped faces of the waveguides are known, the degree of deflection (or the change in deflection) can be calculated using known methods.

In a preferred embodiment, the long axes of the waveguides 400 are substantially collinear at the gap 410 between the cantilever 250 and the first body 100 and the opposed faces of the waveguides are substantially parallel and substantially normal to the collinear long axes of the waveguides. A convenient way of achieving alignment and coupling of waveguides is to fabricate a single waveguide extending across the first and second bodies (including across the cantilever) and thereafter fabricating a gap 410 in the waveguide by machining, etching, or otherwise cleaving the waveguide.

It is immaterial whether the waveguide 400 is fixed to the bodies before or after their fabrication. What is important is that the waveguide that extends along the cantilever 250 is sufficiently fixed thereto or supported thereby that the waveguide deflects when the cantilever deflects.

In another embodiment, the waveguide 400 is not fixed to the second body 200, but instead merely contacts the second body at least at the distal end of the cantilever 250. Deflection of the cantilever (induced by binding of a ligand for a receptor immobilized on the cantilever) causes the cantilever to bend the waveguide, reducing or eliminating its coupling with the waveguide on the first body 100. By way of example, the second body can have a V-shaped groove in which an optical fiber rests. Optionally, a third body, having a similar groove aligned with that of the second body can be urged against the second body, confining the optical fiber in the diamond-shaped space between the second and third bodies.

Further details of the elemental parts of the detector are described in the ensuing sections of this disclosure.

The primary function of the first body 100 is to support the waveguide 400 that extends across it. It is immaterial whether the waveguide is integral with the first body or simply fixed thereto. The first body maintains the waveguide in a position such that when the cantilever 250 is not deflected, the waveguide extending along the cantilever is coupled with the waveguide fixed to or supported by the first body. In operation, it is not important whether the waveguide lies atop (relative to gravity), on the side of, or below the first body, so long as the position of the waveguide is maintained by the first body.

The second body 200 has two functions. First, it anchors the cantilever 250, which extends from the second body. Second, the second body supports the waveguide 400 that extends across it. Like the first body 100, the geometrical orientation of the second body with regard to the waveguide is immaterial. It is also immaterial whether the waveguide is integral with the second body, fixed thereto, or lain across it.

It is important that light conveyed by way of the waveguide(s) 400 extending across the first and second bodies not be significantly transmitted into or absorbed by the bodies. This can be prevented by fabricating the bodies from materials that have a lower refractive index than that of the waveguide material, by interposing a cladding material between the bodies and the waveguide(s), or by forming a distributed Bragg reflector such as that of an anti-resonant waveguide.

Selection of appropriate materials for the first and second bodies and any cladding materials is routine in the art. Substantially any semiconducting substrate known in the art, e.g., crystalline silicon, silicon-on-insulator (SOI), gallium arsenide, indium phosphide, or gallium nitride, can be used to fabricate the first and second bodies. In embodiments in which the cantilever 250 includes a portion made from and integral with the second body material, the resilience of the material used to fabricate the second body 200 must be selected such that deflection of the cantilever is not prevented. Appropriate cladding materials are also known, and substantially any can be used, e.g., silicon dioxide polymers.

In an important embodiment, the first and second bodies are integral parts of a single substrate and are formed by etching, micromachining, or otherwise manipulating the substrate such that the first and second bodies are formed as described in this disclosure. If a detector comprising multiple cantilevers 250 in a common cavity is fabricated from the substrate, it is immaterial whether all cantilevers extend into the cavity from the same side of the cavity. However, for each cantilever, the terminology used in this disclosure refers to the portion of the substrate from which the cantilever extends as the second body 200 and the portion of the substrate on the opposite side of the cavity as the first body 100. Thus, in some multi-cantilever detectors the portion of the substrate that forms the second body for one cantilever may be the same portion of the substrate that forms the first body for another cantilever.

In another embodiment, the first and second bodies are fabricated from separate substrates. The bodies are then arranged so that the waveguide 400 that extend across the bodies are aligned and coupled.

The width of the gap 300 between the first and second bodies is not important. However the gap 300 ought to be made relatively small, e.g., not much longer than the length of the cantilever, in order to minimize the footprint of the device. Smaller gaps 300 can reduce the amount of fluid required to operate the device.

The cantilever 250 extends from the second body 200 of the detector and has a receptor immobilized on, e.g. covalently bound to at least one surface. The cantilever bends when a ligand of the receptor binds with the receptor. The waveguide 400 extending across the second body also extends across the length of the cantilever. In the cantilever's non-deflected condition, i.e., when the cantilever is straight, the waveguide extending along the cantilever is coupled with the waveguide extending across the first body 100. When the cantilever is bent, the two waveguides are no longer coupled or not as efficiently coupled, depending on the degree of deflection from the non-deflected state.

In one embodiment, the cantilever 250 having the receptor bound thereto is in substantially the non-deflected position and the waveguides 400 are coupled; bending of the cantilever induced by binding between the receptor and a ligand decouples the waveguides and decreases transmission of light across the gap 410 between the waveguides. In another embodiment, the cantilever having the receptor bound thereto is bent in the absence of a ligand of the receptor, but straightens to substantially the non-deflected position upon binding between the ligand and the receptor, i.e., whereby the waveguides become coupled. In yet another embodiment, the cantilever having the receptor bound thereto is bent in one direction, e.g., upwardly, in the absence of a ligand of the receptor, but bends in the opposite direction, e.g., downwardly, upon binding between the ligand and the receptor, i.e., whereby the waveguides become transiently coupled.

The cantilever 250 has two substantially planar faces that are substantially parallel to one another. A receptor is immobilized on one of the two faces, but not on the other (or at a much lower concentration on one face than the other). It is immaterial whether the receptor is immobilized on any of the "sides" of the cantilever between the two faces. Preferably, the area of each side is at least an order of magnitude less than the area of the parallel planar faces. Binding of a ligand of the receptor with the receptor induces a surface stress on the face, which is relieved by bending of the cantilever. The direction in which the cantilever deflects depends on whether the surface stress induced upon ligand binding is compressive or tensile. Methods of predicting the direction and degree of deflection are known in the art, e.g., Wu et al., 2001, Proc. Natl. Acad. Sci. USA 98(4):1560–1564; Stoney, 1909, Proc. R. Soc. London Ser. A 82:172; Miyatani et al., 1997, J. Appl. Phys. 81:7099–7115, and selection of reagents and conditions for receptor immobilization are routine.

The waveguide 400 that extends across the second body 200 also extends along the length of the cantilever 250. The waveguide preferably extends along the long axis of the cantilever or of one leg of the cantilever, e.g., along the long axis of a leg of a V-shaped cantilever. However, the waveguide can also extend along an edge or elsewhere along the cantilever. The waveguide can extend along the cantilever substantially parallel with the long axis of the cantilever (or leg thereof) or at substantially any angle up to 45 degrees from the long axis (preferably not more than 30, 20, or 10 degrees from that axis). The waveguide can also extend across, e.g., perpendicular to, the long axis of the cantilever, such that the waveguide on the cantilever is coupled in two places with the waveguide on the first body 100. The waveguide can be located on the face of the cantilever having the receptor immobilized thereon, on the opposite face, on a side of the cantilever, within the cantilever, or any combination thereof.

Depending on the fabrication methods used, the faces of the cantilever 250 may be non-parallel near where the cantilever is anchored to the second body 200. Preferably, at least one parallel face of the cantilever and the portion of the second body to which the cantilever is anchored form a substantially right angle. However, a curved or sloped junction between the cantilever and the second body is acceptable, so long as the portion of the cantilever in which the two faces are substantially parallel is sufficiently large that significant deflection of the cantilever tip occurs upon ligand-receptor binding. Such design is routine, taking into account such factors as the resilience of the cantilever material(s), the surface density of immobilized receptor, the stress expected to be exerted upon the cantilever upon receptor-ligand binding, the thickness and resilience of the waveguide 400 linked with the cantilever, and the like.

In one embodiment, the cantilever 250 is simply the waveguide 400 itself, i.e., with or without claddings. In addition to the waveguide, the cantilever can include a portion of the second body 200, such as a cantilever-shaped portion thereof. Preferably, the thickness of the waveguide measured in the plane normal to the long axis of the cantilever is substantially the same along the length of the waveguide and the thickness of any portion of the second body material in the cantilever is also substantially the same along the length of the cantilever. For example, the cantilever can be a waveguide having a rectangular cross section that is substantially the same along the length of the cantilever. As another example, the cantilever can have the same waveguide fixed to a portion of the second body having a wider (in the plane of the parallel faces) rectangular cross section along the entire length of the cantilever.

The shape of the cantilever 250 is within the discretion of the implementer, and a variety of shapes can be used. The thickness of the cantilever should be substantially uniform along the length thereof. However, some lateral tapering of the cantilever is acceptable, wherein the distal portion of the cantilever is somewhat, e.g., 50%, 25%, 10% or 5%, thinner than the portion of the cantilever where it is anchored to the second body 200. The precise thickness that is desirable for a particular cantilever will depend on the material from which the cantilever is made, i.e., it will depend upon the rigidity, brittleness, and thermal expansion properties of the material, depending on the anticipated conditions of use. In general cantilever thickness will be within the range from 0.1–20 micrometers, and more preferably 0.1–2 or 0.2–0.5 micrometers, e.g., 0.2 micrometer thickness for a silicon cantilever having a length of 500 micrometers and a width of 100 micrometers.

Viewed normal to the plane of the parallel faces, the cantilever 250 can have any of a variety of shapes. In one embodiment, the cantilever is substantially rectangular, with rectangular or rounded distal corners. Viewed along its long axis, the cantilever can have a rectangular, wedge, trapezoidal, or more complex cross-section. The corners at which the cantilever meets the second body 200 can be rectangular, tapered, or rounded, as desired or dictated by the fabrication method. Other acceptable shapes of the cantilever (viewed normal to the plane of the parallel faces) include wedge-shaped, V-shaped (wherein the free ends of the V are anchored to the second body), semicircular, or irregular. If deflections of multiple cantilevers are to be compared, then the cantilevers should be substantially identical in shape and composition.

The length of the cantilever 250 is within the discretion of the implementer, except that it must be sufficiently long that surface stress induced upon binding of a ligand with the receptor immobilized on a surface of the cantilever will deflect the distal end of the cantilever sufficiently that the efficiency of light transmission across the gap 410 between the waveguide linked to the cantilever and the waveguide linked to the first body changes measurably. The length of the cantilever is preferably minimized, in order to facilitate handling during fabrication and operation. Methods of predicting the degree of deflection are known in the art, e.g., Wu et al., 2001, Proc. Natl. Acad. Sci. USA 98(4):1560–1564; Stoney, 1909, Proc. R. Soc. London Ser. A 82:172; Miyatani et al., 1997, J. Appl. Phys. 81:7099–7115. In view of what is known, selection of cantilever and waveguide materials, their thickness, and the surface density of an immobilized receptor are routine design choices. It is understood in the art that tip deflection sensitivity to surface stress scales quadratically with the value (length divided by thickness) and inversely with the biaxial modulus of the cantilever material. By way of example, for a silicon cantilever having a thickness of about 0.2 micrometer and a width of about 100 micrometers, a length of 500–1000 micrometers, i.e., 5–10 times the width) is suitable.

The width of the gap 150 between the distal end of the cantilever 250 and the first body 100 is within the designer's discretion. Preferably, gaps 410 and 150 have the same width and are aligned with one another at each end. The gap 150 should be sufficiently wide that the distal end (including the waveguide 400 that extends along the cantilever) does not contact the first body 100 (or the waveguide extending across it) when the cantilever deflects. The gap 410 should be sufficiently narrow that coupling of light between the end of the waveguide on the distal end of the cantilever and the end of the waveguide on the first body is relatively efficient and insertion loss between the waveguide ends is relatively small, e.g., less than 3 dB, or 50% loss, and preferably less than 1 dB, when the cantilever is in the non-deflected position). Potential thermal expansion or contraction of the cantilever, waveguide, and first and second body materials in the intended temperature ranges of operation and fabrication should be taken into account to avoid expansion-induced contact between the distal end of the cantilever and the first body. The light transmitting properties of the fluid for which the detector is designed should also be taken into account in order to achieve acceptable light coupling between the waveguides. For example, in low index contrast waveguides with a large mode field, a gap of 2–10 micrometers is suitable. In high index contrast waveguides with a small mode field, the insertion loss increases rapidly with increasing gap width, so gaps in such waveguides should be minimized, e.g., 0.4–1 micrometer.

The cantilever 250 has a receptor immobilized on one surface. Typically, many copies of the receptor will be immobilized on the surface (unless the ligand to which the receptor is expected to bind is very large, such as a cell). The surface stress exerted on the cantilever upon binding of the receptor and ligand varies in known ways with the surface density of immobilized receptor, taking into account the type and identity of the ligand. The receptors can be immobilized on the surface of the cantilever using any reagent or chemistry sufficient to maintain immobilization of the receptor on the cantilever under anticipated operating conditions, e.g., in the fluid in which the ligand is to be detected. A skilled artisan is able to select an appropriate immobilizing agent or method based on the identity, desired orientation, and desired surface density of the receptor. Examples of suitable immobilizing agents include silylating agents, thiolating agents, cross-linking agents, and the like.

The cantilever 250 can have a layer of material or a coating which facilitates immobilization of the receptor thereon. By way of example, attachment of polynucleotides and polypeptides can be facilitated by depositing a thin, e.g., 0.5 to 50 nanometer, preferably continuous layer of a metallic element such as gold on a surface of the cantilever. For example, gold can be deposited on all or a portion of the parallel face of the cantilever to which the receptor is to be immobilized. A second metallic layer can be interposed between the elemental metallic layer and the cantilever surface, for example to improve adhesion of the elemental metallic layer to the surface. By way of example, the second metallic layer can include or consist of titanium, chromium, or an alloy of these or other metals.

When the cantilever 250 includes multiple layers of material having significantly different thermal coefficients of expansion, deflection of the cantilever can be induced by temperature changes. For this reason, the temperature of any multi-layered cantilever and any fluid that contacts it are preferably maintained as close as possible, so that any deflection of the cantilever reflects occurrence in the fluid of the ligand, rather than thermal effects. In many embodiments, it is also preferable that the temperature at which the detector is fabricated is as close as reasonably possible to the temperature at which the detector is to be operated.

The differential thermal expansion characteristics of multi-layer cantilevers can also be used as a 'fine-tuning' adjustment for deflection of the cantilever 250. By way of example, if it is desired that the waveguides 400 extending across the first body 100 and across the cantilever and second body 200 be coupled prior to contacting the cantilever with a fluid to be assayed for occurrence of a ligand, then such coupling can be achieved (or maximized) by altering the temperature of the cantilever so that the waveguides are maximally coupled, i.e., so that maximum light transmission efficiency across the waveguide body gap 410 is achieved. If the fluid is maintained at the controlled temperature when it and the cantilever are contacted, then any decrease in light coupling should be attributable to deflection of the cantilever and the sensitivity of the detector should be greater than the sensitivity of a detector in which coupling was not optimized prior to contacting the fluid and cantilever.

The waveguide 400 conveys light from a light source to a light detector and is interrupted by the gap 410 between the portion of the waveguide on the distal end of the cantilever 250 and the portion of the waveguide on the first body 100. If the cantilever is deflected from its non-deflected position, then the ends of the waveguide(s) on either side of this gap 410 become non-aligned and the efficiency of light coupling, i.e., transmission of light across the gap 410 between the ends of the waveguide, decreases. As deflection of the cantilever increases, alignment of the two waveguide portions decreases and the efficiency of light coupling across the gap 410 decreases as well. Because cantilever deflection is associated with receptor-ligand binding, decreased light coupling across the gap 410 can be correlated with occurrence in the fluid of a ligand that binds with the receptor immobilized on the face of the cantilever.

Waveguides 400 extending across the first body 100, the cantilever 250, and the second body 200 are referred to alternatively in the singular and plural tenses in this disclosure. The reason for this grammatical usage is that the waveguide of the detector described herein can be made either as a single waveguide into which a gap 410 is introduced or as separate waveguides that are brought into alignment and separated by a gap 410. Because alignment of microscopic waveguides is much more easily achieved by introducing a gap into an existing waveguide, the waveguides that extend across the first body and across the cantilever and second body are preferably fabricated initially as a single waveguide and thereafter separated from one another (retaining the original alignment) by introducing a gap into the single waveguide to yield a pair of aligned waveguides.

Numerous types of optical waveguides are known in the art. For instance, an optical waveguide can be a elongated substantially rectangular solid formed of a substantially optically transparent material and having a cladding material that exhibits a lower index of refraction than the optically transparent material. Between the clad faces, light is confined within the waveguide by total internal reflection. Between the non-clad faces, light can be confined by shaping the waveguide as a ridge or by total internal reflection. An optical fiber is a specialized form of an optical waveguide in which the waveguide has the form of an elongated cylinder of a substantially optically transparent material clad within a material having a lower refractive index, wherein the difference in the refractive index makes the fiber suitable for conveying light from one end of the material to the other by total internal reflection.

The waveguide 400 can be an integral portion of the first and second bodies and the cantilever 250 or it can be a separately fabricated device which is fixed to the first and second bodies and the cantilever, although the former is preferred. The waveguide can be integral with or fixed to a surface of the bodies and the cantilever. Alternatively, the waveguide can be contained within, or encased by, one or more of the bodies and the cantilever, e.g., the second body 200, the cantilever, or both, can encase the waveguide.

If the waveguide 400 is integral with one of the bodies or the cantilever 250, a cladding material having a lower index of refraction than the waveguide material must be selected to prevent leakage of light into the first and second bodies. The waveguide and the cladding materials can be an integral part of a single material. For example, a silicon-on-insulator substrate can be used, wherein a silicon oxide layer is interposed between a silicon waveguide core and the bulk material of the first and/or second bodies. Alternatively, the cladding and core layers can be added to the first and second bodies, e.g., by depositing layers of silicon dioxide as a cladding and silicon oxynitride as the waveguide core.

The material from which the waveguide 400 is fabricated can be any material that is suitable for use as an optical waveguide. Typically, an absorption loss of less than 0.5 decibel per centimeter is considered desirable. However, when relatively short waveguides are used, higher absorption loss values are tolerable. A wide variety of such materials are known, including semiconducting materials, dielectric materials (including various glasses), and plastic materials. Specific examples of suitable materials include minerals such as silicon, silicon nitrides, silicon oxynitrides, silicon dioxides, gallium arsenide, indium phosphide, and mixtures thereof and polymers such as polycarbonates, polyimides, and polymethacrylates.

Light loss from an optical waveguide 400 can be decreased by coating, encasing, or contacting the waveguide with a cladding material. A cladding material is a material which exhibits a lower (preferably much lower; e.g., more than 10% lower) index of refraction than the waveguide material. When light conveyed by the waveguide contacts the boundary between the waveguide and the cladding material, the light is reflected within the waveguide material, rather than transmitted into or absorbed by the cladding. The cladding material can be applied to or synthesized on the surface of the waveguide. Alternatively, the surface of the waveguide can be treated, e.g., to lower the refractive index of the surface layer of the waveguide material such that an integral cladding layer is formed. Cladding materials and methods are known in the art and choice of a particular method or material is simply a routine design decision made taking into account the identity of the waveguide material, the identity of the materials that the waveguide contacts, the environment in which the detector will be used, and other known factors.

In one embodiment of the detector disclosed herein, the waveguide 400 is coated with a cladding material along at least a portion of its length, e.g., the portion extending across the first body 100, the portion extending across the second body 200 to the anchor point of the cantilever 250, the portion extending along the cantilever, or some combination or part of these. For example, the detector may have cladding on all portions of the waveguide except the portion extending along the cantilever.

When the cantilever 250 is in its non-deflected position, the end of the waveguide 400 fixed to the first body 100 adjacent the gap 300 between the first and second bodies should be aligned with the end of the waveguide fixed to the distal end of the cantilever. In this aligned position, light should be efficiently transmitted between the waveguide of the cantilever and the waveguide of the first body. Such transmission can be affected by the geometry of the ends of the waveguides. The geometry should be such that most light exiting the end of one waveguide enters the end of the other waveguide. Thus, the waveguide ends should be spaced sufficiently close that most light exiting the end of one waveguide is cast upon the end of the other waveguide. Such spacing depends on the composition and size of the waveguides, and appropriate spacing is merely a routine design decision. For ease of fabrication and reduction of light loss, the ends of the waveguides are preferably butt-gapped, i.e., substantially planar and parallel to one another, and are more preferably also substantially normal to the long axis of the waveguide.

The ends of the waveguide(s) 400 distal from the gap 410 between the cantilever 250 and the first body 100 are coupled with a light source and a light detector to facilitate light transmission from the light source, through the waveguide(s), to the detector. It is immaterial in which direction light transmission across the gap 410 occurs, i.e., whether from the first body toward the cantilever or vice versa. The function of the light source and the detector is to provide a detectable signal that can be affected by deflection of the cantilever. Receptor-ligand binding affects deflection of the cantilever, which affects alignment of the waveguide ends adjacent the gap 410 between the cantilever and the first body. If the ends are not aligned, light cannot be transmitted from the source to the detector. If the ends are aligned, light transmission from source to detector can occur, and the amount of transmitted light is affected by the degree of alignment. Thus, light transmission from source to detector can be correlated with occurrence (or concentration) of ligand in a fluid contacted with the cantilever.

A wide variety of light sources, e.g., lasers and light emitting diodes (LEDs), are known, and substantially any source can be used as a light source for the detector described herein. The light transmitted through the waveguide 400 can be substantially monochromatic, e.g., light emitted from a laser, or polychromatic, e.g., light emitted from an LED. Regardless of the light source, light from the source must be coupled with the waveguide. The wavelength of light conveyed in the detector is not important. Wavelengths in the visible range of the electromagnetic spectrum can be used, as can wavelengths in the infrared and ultraviolet ranges. Choice of an appropriate wavelength or combination of wavelengths is a routine design decision based on the properties of the waveguide used, any absorbance of the fluid to be assayed, the availability and cost of light sources and detectors, and the like.

The means used to couple light from a source into the waveguide 400 can be substantially any means suitable for this purpose. Many ways of directing, focusing, and transmitting light into an optical waveguide are known, and substantially any of those ways can be used to couple light from the source into the waveguide. In one embodiment, the light conveyed by the waveguide is simply incident light from the source that falls upon the end of the waveguide at an angle less than the cutoff angle characteristic of the waveguide and is thereafter conveyed within the waveguide. In other embodiments, a lens is used to improve coupling efficiency. Alternatively, a grating formed in the waveguide or a prism can be used to couple light into the waveguide. Such technologies are known, and selection of a means for conveying light from a source into the waveguide is a routine design choice.

The choice of a light detector and means for conveying light transmitted through the waveguide 400 of the detector to that light detector are within the discretion of the implementer. A wide variety of light detectors are available, including photodiodes, photomultipliers, photosensitive films, and light-reactive chemicals. Light conveying means include butt-coupling or evanescent coupling of the waveguide with the detector. Coupling efficiency can be improved using a lens. Alternatively, a grating can be formed in the waveguide to extract light from the waveguide and direct it toward the detector. Selection of an appropriate light detector and any means of conveying light from the waveguide of the detector described herein to the light detector is a routine design choice.

The light source and the light detector can each be fixed to the detector or separate therefrom. In one embodiment, the light source, first and second bodies, cantilever, and waveguide are fabricated on a single substrate, on which the light detector can alternatively also be fabricated. In another embodiment, the first and second bodies, cantilever, and waveguide are fabricated on a single substrate and portions of the substrate are adapted to couple light from an external source into the waveguide and to couple light transmitted through the waveguide, i.e., across the gap 410 between the portion of the waveguide 400 on the cantilever 250 and the portion of the waveguide 400 on the first body 100, into or toward an external light detector. In this latter embodiment, the detector can be mass produced as a disposable assay component and the more intricate and expensive light source and detector components can be housed in one or more instruments adapted for use with the detector.

The light source and sensor can be operated continuously, periodically, or intermittently, as desired. In one embodiment, the light source is activated continually following contact of the fluid and the cantilever, and measurements are made substantially continuously, e.g., microseconds, milliseconds, seconds, or minutes apart. In that embodiment, light transmission associated with the initial, intermediate, and equilibrium positions of the cantilever 250 can be assessed, and the rate of cantilever deflection can be accurately calculated or estimated during the period of deflection. In another embodiment, the light source and detector are activated prior to contacting the cantilever with the fluid, in order to maximize light transmission and "fine tune" the cantilever to the most-coupled position, e.g., by manipulating the temperature of the cantilever and fluid. Thereafter, the fluid and cantilever are contacted and permitted to achieve equilibrium, e.g., by maintaining the contact for 1, 2, 4, or 8 hours or more. Thereafter, the light source and detector are activated in order to assess the degree of light coupling, i.e., the position of the cantilever, at equilibrium.

In prior art cantilever-based detectors wherein light is reflected or diffracted off from the surface of a cantilever and the reflected or diffracted light is assessed, it is known that there are at least two modes of assessing a surface stress on the cantilever. In the first method, a change in the position of reflected light or a change in the wavelength or position of diffracted light is assessed, the change being due to the position of the cantilever, which is altered upon binding of a ligand to the receptor immobilized on the cantilever. In the second method, regular vibration of the cantilever is induced, e.g., by mechanical or acoustic excitation of the cantilever or by magnetic excitation of a magnetically coated cantilever; see, e.g., Tamayo et al., 2001, Ultramicroscopy 86:167–173. The vibration can be induced by a device coupled with the cantilever, i.e., contacting or otherwise communicating with the cantilever in a way that energy from the device induces vibration of the cantilever. The cantilever exhibits a characteristic resonant frequency, which can be assessed using known methods (see Tamayo et al., supra, for example). A change in surface stress associated with binding of a ligand to the receptor immobilized on the cantilever can be detected as a change in the resonant frequency of the cantilever upon ligand binding.

These same two modes of assessing cantilever surface stress can be readily adapted to the light detector output obtained using the detector described herein. Thus, either a change in the deflected position of the cantilever 250 (as assessed by the final efficiency of light transmission from the light source to the detector) or a change in the resonant frequency of the cantilever (as assessed by the resonant frequency of light intensity measured with the detector) can be used to assess ligand receptor binding in the detector described herein.

Numerous examples of receptor-ligand pairs are known in the art, including antibodies and their corresponding antigens, proteins and ligands, e.g., other proteins, other copies of the same protein, and relatively small enzymatic substrates, with which they bind, complementary nucleic acids, and the like. In the context of this disclosure, it is immaterial which molecule of a receptor-ligand pair is designated the "receptor" and which is designated the "ligand." Typically, if one molecule of the pair is much larger than the other then it is designated the receptor and the smaller molecule of the pair is designated the ligand. In this disclosure, however, the member of the pair that is immobilized on the cantilever surface is designated the receptor and the molecule that binds with it is designated the ligand. Thus, although a small molecule that binds with a protein would typically be designated a ligand of the protein, that molecule is designated the receptor if it is bound to the surface of a cantilever of a detector described herein and the protein is referred to herein as the ligand of the cantilever-bound molecule.

The receptor immobilized on the face of the cantilever 250 can be substantially any molecule that specifically binds with a ligand that one desires to detect in a fluid. The receptor can be one that will bind substantially only a single ligand, e.g., a monoclonal antibody that binds specifically with only a single antigen or a substrate or substrate analog of an enzyme. Alternatively, the receptor can be one which will bind a small or large group of ligands, such as a monoclonal antibody that binds specifically with an epitope common to multiple antigens or a substrate or substrate analog of a family of enzymes, e.g., glucose or a glucose analog. Examples of suitable receptors include molecules that bind with polypeptides, polynucleotides, carbohydrates, cells, or combinations of these. Such receptors include polypeptides, polynucleotides, carbohydrates, cells, and relatively small molecules, e.g., organic compounds having molecular weights less than 10,000 Daltons, preferably less than 1,000 Daltons.

In one embodiment, the receptor is a polynucleotide having a selected nucleotide sequence. Under solution conditions (e.g., ionic strength, ligand concentration, temperature, and time of incubation) that can be predicted or assessed using known methods, the receptor polynucleotide will hybridize, i.e., anneal, with another polynucleotide, i.e., a ligand of the receptor, that has a nucleotide sequence that includes a portion complementary to the nucleotide sequence of the receptor. It is also known that controlling the solution conditions, e.g., temperature, ionic strength, and detergent concentration, in known or readily discernable ways will cause the receptor polynucleotide to fail to bind with polynucleotides having sequences that are nearly, but not quite, complementary to the receptor nucleotide sequence. Thus, the receptor selected in this embodiment of the detector described herein can be used to determine whether a polynucleotide having a particular sequence occurs in a liquid sample.

For example, a detector can include multiple cantilevers 250, each having identical single-stranded polynucleotides immobilized thereon. The sequences of the immobilized polynucleotides can be selected to be complementary with (or homologous to) overlapping portion of a nucleotide sequence that naturally occurs. The sequences can also be selected such that, under the conditions at which the fluid is to be contacted with the cantilevers, the immobilized polynucleotides will not hybridize substantially with a sample polynucleotide unless the sample polynucleotide includes a portion having a sequence that is exactly complementary with the immobilized polynucleotide sequence. In such a device, a cantilever will deflect if the sample polynucleotide includes the complementary sequence, but will not deflect if the sample polynucleotide does not include that sequence. Using such a device, portions of a sample polynucleotide that have a sequence different from the naturally occurring sequence can be identified. By way of example, a detector having 20-residue polynucleotides immobilized on its cantilevers such that the polynucleotide sequences overlap with one another by 19 residues, i.e. representing all possible 20-mers in an anticipated sequence such as a gene, can be used to detect single-residue or multiple-residue differences between a sample sequence and the anticipated sequence.

In another embodiment, the receptor is a monoclonal antibody that binds specifically with substantially only a single antigen (or perhaps with fragments of the antigen that include the epitope of the antibody). This embodiment of the detector is useful for detecting occurrence of the antigen (or a fragment of the antigen) in a fluid. The antigen can be substantially any structure that can be bound specifically by an antibody, including for example a cell, e.g., human, animal, plant, or microbial, a protein, a polynucleotide, a carbohydrate, a virus, a drug, a hormone, or an eicosanoid. Alternatively, the antigen can be immobilized on the cantilever face (as the receptor) and the resulting detector can be used to assess a liquid sample, e.g., a human blood, serum, urine, saliva, or bronchial lavage sample, for occurrence of an antibody, i.e., the ligand of the antigen receptor, that binds specifically with the antigen.

In yet another embodiment, the receptor and ligand are a lectin, i.e., a carbohydrate-binding protein, and a carbohydrate with which the lectin specifically binds. The ligand can be on the surface of a cell, on the surface of a membrane fragment, on a protein, or free in suspension. Either of the lectin and the carbohydrate can be used as a receptor and immobilized on the surface of the cantilever 250 using known methods. The resulting detector can be used to assess occurrence of the other of the lectin and the carbohydrate in a fluid.

The density at which the receptor should be immobilized on the surface of the cantilever 250 depends on a number of factors, including the mode in which the detector is to be operated, the surface stress exerted on the cantilever surface upon receptor immobilization, the effect of receptor-ligand binding on surface stress, and any difference between the immobilization temperature and the anticipated temperature of operation of the detector. These factors can be assessed and selected by a skilled artisan to determine an appropriate receptor surface density.

The detector described herein can be used to detect a ligand in substantially any fluid with which the cantilever surface having the receptor immobilized thereon can be contacted. The fluid can be a liquid, a gas, a gel, or the like. It is important that the viscosity of the liquid not be so great that deflection of the cantilever 250 induced upon receptor-ligand binding is prevented.

In one embodiment, the fluid is a aqueous suspension of biomolecules derived from a biological source. By way of example, the fluid can be a blood, serum, urine, saliva, or bronchial lavage sample. These fluids can be used directly or subjected to one or more purification procedures to separate components thereof. Alternatively, a suitable fluid can be a suspension made by breaking cells and suspending their contents in an aqueous liquid. As another example, a suitable fluid can be a suspension of DNA molecules generated by amplification, e.g., by PCR, of one or more nucleic acids present in a biological sample.

In detectors in which the cantilever(s) 250 is made from more than one material, e.g., the optical waveguide 400, the second body 200, and one or more metallic coatings, the liquid and the detector are preferably maintained at substantially the same temperature, e.g., ±0.25 degree Celsius, preferably ±0.05 degree Celsius, in order to minimize cantilever deflection attributable to differences in the thermal expansion coefficients of the components of the cantilever(s).

Other desirable characteristics of the fluid include that it does not have solids suspended therein that are sufficiently large to clog fluid channels within the detector and that it does not include materials which interfere significantly with light coupling between the optical waveguide 400 of a cantilever 250 and the corresponding optical waveguide of the first body 100 when the cantilever is in the non-deflected position.

The detector described herein can have a single cantilever 250 or multiple cantilevers 250. When the detector has multiple cantilevers, all of the cantilevers can have the same receptor bound thereto, all of the cantilevers can have different receptors bound thereto, or multiple individual cantilevers can have different individual receptors bound thereto. These arrangements permit multiple measurements for a single receptor using a single detector and provide robustness to the device, e.g., redundancy in the event a cantilever corresponding to a receptor breaks off or is malformed during production of the detector. Multiple cantilevers and their corresponding waveguides can be arranged in parallel, i.e., an individual waveguide split across multiple cantilevers, in series, i.e., a single, multiply-gapped waveguide extending across several cantilevers, or some combination thereof.

By way of example, a substrate can be manipulated to form a single large gap 300 into or across which a plurality of cantilevers 250 extend. For each cantilever, the portion of the substrate from which the cantilever extends is the second body 200, and the portion of the substrate distal to the cantilever, i.e., on the other side of the cavity, is the first body 100. In this example, all cantilevers can extend from one edge of the cavity toward the other or some can extend in one direction and the others in the opposite direction.

Further by way of example, a substrate can be manipulated to form one or more gaps 300, wherein only a single cantilever 250 extends into each cavity.

In a detector having multiple cantilevers 250, the cantilevers need not be identical to one another in shape or size. For example, a detector can have a plurality of substantially rectangular cantilevers (viewed normal to the plane of the parallel faces of the cantilevers) which have various widths, i.e., measured perpendicular to the long axes of the cantilevers, but substantially the same length and thickness. Because less surface force is required to deflect the narrower cantilevers, such a detector can be used to assess the concentration of a ligand in a fluid over a wider range of concentrations than would otherwise be possible using a detector having cantilevers of only one width therein.

In a multiple-cantilever detector, each cantilever 250 has at least one optical waveguide 400 fixed thereto, and that waveguide transmits light to a corresponding waveguide fixed to the first body 100. Each individual waveguide 400 can be separately coupled with a light source, e.g., a laser illuminating an array of grooves etched in the waveguide. Alternatively, multiple waveguides can share a common light source. By way of example, the waveguides fixed to multiple cantilevers can be joined at a single source waveguide. Light from the light source can be delivered to the source waveguide and distributed among the various waveguides 400 joined thereto. Alternatively, light from a tunable wavelength light source, e.g., a laser, can be demultiplexed among various waveguides. Similarly, the waveguides fixed to the first body and corresponding to various individual cantilevers can be joined at a single outlet waveguide. Preferably, the waveguides corresponding to an individual cantilever are joined with others at only one side of the first body-second body gap 300, so that deflection of the cantilever can be assessed independently of other cantilevers.

In one embodiment of the detector described herein, a single light source is used, and light is provided to each cantilever 250 of the device by way of an optical splitter. In this embodiment, light transmitted across the gap 410 is conveyed by a separate outlet waveguide 400 for each cantilever, and light conveyed by each outlet waveguide is individually assessed. The conveyed light can be assessed using one or more light detectors. For example, individual light detectors can be positioned to detect light conveyed past each cantilever, or a single light detector, with appropriate mechanical positioning or optical reflection/refraction apparatus, can be used to individually detect light conveyed past each cantilever.

In another embodiment, each cantilever 250 of a detector has an individually addressable light source waveguide 400, and all of the waveguides conveying light transmitted across the gaps 410 are joined into a common outlet waveguide. Deflection of individual cantilevers is assessed by providing light to the corresponding light source waveguide and detecting light at the common outlet waveguide.

In still another embodiment, the waveguides 400 corresponding to a plurality of cantilevers 250 are joined to both a common light source waveguide and a common outlet waveguide. The cantilevers have different widths or thicknesses, but are otherwise substantially identical. Light is provided to each of the pluralities of cantilevers by way of the common light source waveguide, and the intensity of light at the common outlet waveguide is assessed in order to determine how many of the waveguides are deflected. This embodiment is useful for assessing the concentration in the fluid of a ligand of the receptor immobilized on the cantilevers.

In each of the foregoing embodiments, it is immaterial to which side of the waveguide gap 410 light is applied. Light transmitted across the gap 410 from one side should be assessed on the opposite side.

The detector described herein can be fabricated using substantially any method known in the art of making microscopic devices. Such methods include micromachining, etching, deposition, and combinations thereof, for example. Generally, the receptor will be immobilized on a surface of the cantilever 250 only after the cantilever has been fabricated, in order to reduce mixing of receptors from different cantilevers. However, especially when all cantilevers are to have the same receptor immobilized thereon, the receptor can be immobilized on a surface before the surface is manipulated to form separate individual cantilevers.

The first and second bodies are preferably fabricated from a unitary substrate, because this permits relatively easy alignment of surfaces of the first and second bodies. Alternatively, separate substrates can be used to fabricate each of the first and second bodies. If the bodies are separately formed, a surface of the first body 100 is preferably aligned with a surface of the second body 200 prior to forming or fixing one or more waveguides 400 thereon.

The waveguides 400 can be fabricated in place on a portion of the first and second bodies, i.e., the second body 200 including the cantilever 250, or fabricated separately and later fixed to the first and second bodies. Because both i) attachment of a prefabricated waveguide to an existing cantilever structure and ii) fabrication of a cantilever structure around the attachment site of a prefabricated waveguide can be difficult, the waveguide is preferably fabricated in place. The waveguide can be fabricated on a surface of the first and second bodies prior to or after fabrication of the cantilever structure. By way of example, a waveguide can be fabricated on a surface of a unitary substrate and first and second bodies and the corresponding cantilever can thereafter be fabricated from the substrate having the waveguide in place. Alternatively, steps involved in fabrication of the waveguide can be interspersed with steps involved in fabrication of one or more of the first and second bodies and the cantilever.

In one embodiment of a fabrication method, a unitary substrate is machined or etched to form a substantially flat surface. A waveguide 400 is fixed to or deposited on the surface. A gap is introduced into the substrate and waveguide, normal to the surface of the substrate and normal to the long dimension of the waveguide. The gap can extend completely through the substrate or, preferably, only part of the way through, so that the first and second bodies are fixed in place relative to one another by the remaining substrate. The gap separates the first and second bodies, forms the gap 150 between the distal end of the cantilever 250 and the first body 100, and forms the gap 410 in the waveguide. The second body portion of the substrate is further eroded to form the outline (viewed from above) of the cantilever. The substrate is eroded throughout its thickness, so that the cantilever at this stage has substantially the same thickness as the original substrate, but extends only from the second body portion of the substrate. The face of the cantilever opposite the face on which the waveguide is fixed is eroded until the desired thickness is obtained. The receptor is immobilized on one face of the cantilever. A skilled artisan understands that many alternative fabrication schemes can be used in place of this one.

The detector described herein can be used to assess occurrence in a fluid of a ligand that binds specifically with a receptor. The receptor is bound to at least one cantilever 250 of the detector, and occurrence of the ligand in the fluid is assessed by contacting the cantilever with the fluid and assessing deflection of the cantilever. If the ligand is present, it will bind with the receptor and exert (or relieve) a surface stress on the cantilever, thereby inducing deflection of the cantilever. Deflection of the cantilever is assessed by assessing light coupling between a waveguide 400 on the cantilever 250 and a waveguide 400 on the first body 100. Such light coupling is maximized when the cantilever is in the non-deflected position, and decreases predictably with increased cantilever deflection.

A variety of appropriate assay format are apparent to skilled artisans. For example, the detector described herein can be used to directly detect occurrence of a ligand in a fluid by contacting a cantilever 250 of the detector having a corresponding receptor bound thereto with the fluid and assessing deflection of the cantilever. Alternatively, occurrence of a competitive inhibitor of receptor-ligand binding in a sample fluid can be assessed by comparing deflection of the cantilever in the presence of the ligand and in the presence and absence of the sample fluid. In the presence of the ligand and a competitive inhibitor of the receptor, deflection of the cantilever will occur to a lesser degree than occurs in the presence of the ligand and the absence of the inhibitor. The inhibitor can, for example, be the receptor itself, i.e., in the sample fluid, not the receptor molecules immobilized on the cantilever face, an analog of the receptor, or a different molecule that binds with or sequesters the ligand in the fluid provided to the detector.

EXAMPLES

The invention is now described with reference to the following Examples. These Examples are provided for the purpose of illustration only, and the invention is not limited to these Examples, but rather encompasses all variations which are evident as a result of the teaching provided herein.

Fabrication of a Multiple Cantilever Detector

This example describes how a detector described herein can be fabricated.

A double-sided polished silicon wafer having a substantially uniform thickness of about 250 micrometers is used as a substrate. The silicon substrate is immersed in a boiling 6:1:1 mixture of distilled, de-ionized water (DDW):ammonium hydroxide:hydrogen peroxide. After rinsing, the substrate is immersed in a boiling bath of a 6:1:1 mixture of DDW:hydrochloric acid:hydrogen peroxide in order to clean the surface thereof. After rinsing with DDW, the wafer is immersed in concentrated hydrofluoric acid for 5 minutes. The wafer is rinsed again with a copious amount of DDW and then dried under a stream of a non-reactive gas, such as nitrogen or argon. This process is referred to as an RCA clean.

A layer of silicon dioxide is formed on the surface of the wafer by maintaining the wafer at about 1000 degrees Celsius under wet oxygen flow for several hours. Subsequently, single mode waveguides are deposited using plasma enhanced chemical vapor deposition (PECVD) to apply silicon oxynitride (SiON), followed by patterning and etching of ridge structures. The SiON core is encapsulated with a PECVD-deposited cladding of silicon dioxide. The wafer is subjected to a second RCA clean, after which a thin (ca. 1500 Angstrom) low stress silicon nitride film is deposited by low pressure vapor deposition. The nitride film serves as an etch mask for KOH etching. The wafer is cooled and the silicon nitride/oxide is removed from the back side of the wafer. The wafer is immersed in a 70% (w/v) solution of KOH and maintained at about 40 degrees Celsius until all of the substrate is removed, leaving a suspended waveguide membrane. Subsequently, the silicon nitride etch mask can be stripped.

The front side of the wafer is then coated with a photoresist mask in a pattern that defines the cantilever, first body, and second body (which are covered by the photoresist) and the gaps therebetween (which are not covered by the photoresist), and the wafer is exposed. The aluminum-coated wafer is then subjected to reactive ion etching to remove portions of the wafer not coated with the photoresist. The face of the cantilever is coated with a thin (20 nanometer) layer of gold, on which biological molecules, e.g., single-stranded polynucleotides, can be immobilized.

Example of Appropriate Cantilever Dimensions

Cantilever distal tip deflection sensitivity to surface stress scales i) quadratically with the value (length divided by thickness) and ii) inversely with the biaxial modulus of the cantilever beam. Using a silicon cantilever having a rectangular cross section wherein the cantilever has a length of 500 micrometers in its long dimension, i.e., anchor to distal tip, a width of 100 micrometers, and a thickness of 1 micrometer, the stiffness of the cantilever will be about 10 milliNewtons per meter. Thus, an induced surface stress of 5 milliNewtons per meter could be expected to deflect the tip of this cantilever by about 20 nanometers. If the thickness of the cantilever were reduced by a factor of three, i.e., to about 330 nanometers, then an induced surface stress of 500 microNewtons per meter could be expected to produce about the same degree of cantilever tip deflection.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

We claim:

1. A detector for detecting a ligand in a fluid, the detector comprising
   a first body;

a second body having a cantilever extending therefrom into a gap between the first and second bodies, the cantilever having two substantially parallel planar faces, wherein one of the planar faces has a receptor that binds specifically with the ligand immobilized thereon; and a gapped optical waveguide extending across the first and second bodies and along the length of the cantilever, wherein the gap of the waveguide coincides with the gap between the first body and the distal end of the cantilever, whereby binding of the ligand with the receptor induces bending of the cantilever, thereby misaligning the gapped ends of the waveguide and decreasing light coupling across the gap of the waveguide.

2. The detector of claim 1, wherein the waveguide is integral with the cantilever.

3. The detector of claim 1, wherein the fluid is one of a liquid and a gas.

4. The detector of claim 1, wherein the waveguide comprises a material selected from the group consisting of a semiconducting material, a dielectric material, and a polymer.

5. The detector of claim 1, wherein the second body comprises a cladding material for the waveguide.

6. The detector of claim 5, wherein the first body also comprises the cladding material.

7. The detector of claim 6, wherein the waveguide contacts the cladding material along substantially its entire length, except for the portion of the waveguide on the cantilever.

8. The detector of claim 1, wherein the first and second bodies are integral parts of a single substrate.

9. The detector of claim 1, wherein a first metallic layer is interposed between the receptor and the face of the cantilever.

10. The detector of claim 1, wherein the cantilever has a shape selected from the group consisting of substantially rectangular, wedge-shaped, and V-shaped, when viewed normal to the plane of the planar faces.

11. The detector of claim 1, wherein the second body has a plurality of the cantilevers extending therefrom into the gap between the first and second bodies, and wherein at least one gapped waveguide extends across the first and second bodies along the length of each of the plurality of cantilevers, the gap of each waveguide coinciding with the gap between the first body and the distal end of the corresponding cantilever.

12. The detector of claim 11, wherein at least two of the cantilevers individually have receptors for different ligands immobilized on the face thereof, whereby binding of one of the ligands with its receptor induces bending of the corresponding cantilever and misalignment of the gapped ends of the waveguide extending along the length of that cantilever.

13. The detector of claim 1, wherein the ligand is selected from the group consisting of cells, polypeptides, polynucleotides, carbohydrates, and combinations of these.

14. The detector of claim 13, wherein the ligand is a first polynucleotide.

15. The detector of claim 14, wherein the receptor is a second polynucleotide having a nucleotide sequence complementary to the nucleotide sequence of the first polynucleotide.

16. The detector of claim 1, wherein the receptor is a polynucleotide.

17. The detector of claim 1, wherein the receptor is a polypeptide.

18. The detector of claim 17, wherein the polypeptide is an antibody.

19. The detector of claim 1, wherein the ends of the waveguide distal from the gap therein are coupled with a light source and a light detector.

20. The detector of claim 1, further comprising a device coupled with the cantilever for inducing a regular vibration of the cantilever, whereby the frequency of vibration of the cantilever can be assessed by the frequency of light coupling across the gap of the waveguide and whereby binding between the ligand and the receptor alters the resonant frequency of vibration of the cantilever.

* * * * *